Feb. 5, 1957 E. H. DOERR Plant Pat. 1,559
DOUBLE GLADIOLUS PLANT
Filed Feb. 2, 1956
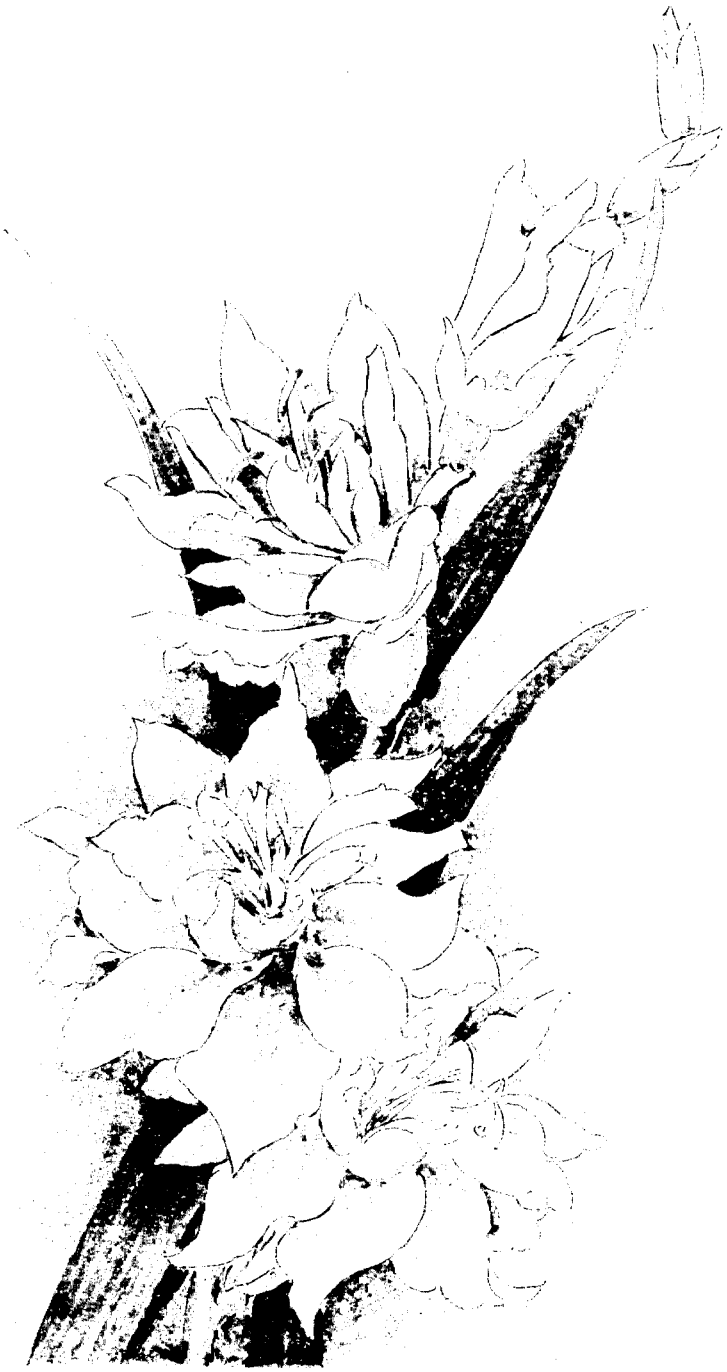
WITNESS
Addison E. Avery
INVENTOR
ERVIN H. DOERR
by Rummler, Rummler & Luow
ATTYS.

United States Patent Office

Plant Pat. 1,559
Patented Feb. 5, 1957

1,559

DOUBLE GLADIOLUS PLANT

Ervin H. Doerr, New Ulm, Minn.

Application February 2, 1956, Serial No. 563,157

1 Claim. (Cl. 47—60)

This discovery concerns a new and distinct variety of double gladiolus plant, originated by me at New Ulm, Minnesota, as the result of crossing the variety "Red Charm" (not patented), as the seed parent, with a variety identified as "Multipetal #1" (not patented), as the pollen parent. I have identified this new variety as Seedling 061–4 in my breeding work.

As the result of this breeding, the novelty of my new variety resides primarily in the depth, brilliance and uniformity of color of the flowers, the very double form of its blooms, and its vigorous growing habit.

My new variety is distinguished and outstanding from its parent and all other known varieties by its prolific petalage. Standard gradioli varieties have six petals, while this seedling bears 18 petals to each bloom. This abundant quantity of petals, its inflorescense on the peduncles, its spikes of medium length, and its intense red coloring make it most desirable for floral work; and these conspicuous characteristics give the flowers an unusual pliability for arrangement in floral pieces and make it a spectacular commercial product.

This new variety has been asexually reproduced by me for several years, at New Ulm, Minn., from cormels grown into blooming size bulbs and I have established that characteristics and distinctions come true to form and are apparently permanently fixed.

The accompanying painting shows the approximate form of my new double gladiolus together with its structure and its distinctive coloring.

The following is a detailed tabular description of this new variety.

Parentage: Seedling.
*Seed parent.*—"Red Charm."
*Pollen parent.*—"Multipetal #1."

Flower:
*Blooms.*—Once—in midseason.

*Size.*—Medium.
*Petalage.*—18 petals on each floret.
*Form.*—Long; somewhat serrated.
*Color.*—Outer petals: Red; inner petals: Red. Base: Red. Reverse side: Red.
*Appearance.*—Velvety.
*Persistence (hang on and dry).*—Fair.
*Lasting quality.*—On plant: fair; as a cut flower: fair.

Bud:
*Size.*—Average.
*Form.*—Average globular.
*Color.*—When sepals first divide: Red; when petals begin to unfurl: Red.

Plant:
*Height.*—Average.
*Growth.*—Good.
*Size of leaf.*—Medium. Produces usual corns.

Genital organs:
*Stamens, anthers.*—Normal. Length: average.
*Number.*—3.
*Color.*—Red.
*Arrangement.*—Normal.
*Pollen.*—Red.
*Ovaries.*—Abnormal.
*Styles.*—One, with 3 white tipped stigmas.

The color designations according to "A Dictionary of Color by Maerz and Paul" are as follows:

| | Plate | Letter | No. |
|---|---|---|---|
| Flower: | | | |
| Main red large petals | 1 | L | 10 |
| Smaller center petals | 2 | I | 7 |
| to | 2 | J | 7 |
| Larger center petals | 2 | G | 9 |
| to | 2 | J | 9 |
| Pistil: | | | |
| Single style—3 branched at upper end. White at bottom, pink at upper end | 1 | I | 7 |
| Stamens: | | | |
| 3—Pink stem | 1 | I | 7 |
| tipped with | 4 | I | 4 |
| Main leaf—green | 21 | J | 6 |
| to | 21 | J | 8 |

Having thus disclosed my invention I claim:

A new and distinct variety of double gladiolus plant substantially as shown and described, characterized as to novelty by the brilliant red coloring of the bloom, the unusually large number of petals comprising each floret, the compactness of its flower formation on a medium length stem, and its good growth to a medium heighth.

No references cited.